US012667351B2

(12) United States Patent
Dale et al.

(10) Patent No.: US 12,667,351 B2
(45) Date of Patent: Jun. 30, 2026

(54) ASSEMBLY AND METHOD FOR THE CLOSURE OF VASCULAR ABNORMALITIES

(71) Applicant: St. Jude Medical, Cardiology Division, Inc., St. Paul, MN (US)

(72) Inventors: Theodore P. Dale, Corcoran, MN (US); Tracee Eidenschink, Wayzata, MN (US)

(73) Assignee: ST. JUDE MEDICAL, CARDIOLOGY DIVISION, iNC., St. Paul, MN (US)

( * ) Notice: Subject to any disclaimer, the term of this patent is extended or adjusted under 35 U.S.C. 154(b) by 195 days.

(21) Appl. No.: 18/471,649

(22) Filed: Sep. 21, 2023

(65) Prior Publication Data

US 2024/0115248 A1     Apr. 11, 2024

Related U.S. Application Data

(60) Provisional application No. 63/414,158, filed on Oct. 7, 2022.

(51) Int. Cl.
*A61B 17/00* (2006.01)

(52) U.S. Cl.
CPC ................................ *A61B 17/0057* (2013.01); *A61B 2017/00592* (2013.01); *A61B 2017/0061* (2013.01); *A61B 2017/00619* (2013.01); *A61B 2017/00623* (2013.01); *A61B 2017/00659* (2013.01); *A61B 2017/00681* (2013.01); *A61B 2017/00867* (2013.01); *A61B 2017/00982* (2013.01)

(58) Field of Classification Search
None
See application file for complete search history.

(56) References Cited

U.S. PATENT DOCUMENTS

| | | | | | |
|---|---|---|---|---|---|
| 5,171,259 A | * | 12/1992 | Inoue | ................. | A61B 17/0057 606/232 |
| 7,753,934 B2 | * | 7/2010 | Wilk | .................... | A61B 17/085 606/213 |
| 2005/0256532 A1 | * | 11/2005 | Nayak | ................. | A61B 17/0057 606/151 |

(Continued)

FOREIGN PATENT DOCUMENTS

WO          2022100832 A1      5/2022

*Primary Examiner* — Jing Rui Ou
(74) *Attorney, Agent, or Firm* — SLEMAN & LUND LLP

(57) ABSTRACT

Described herein is a patch delivery assembly for treating a target site and a method for deploying the same. The patch delivery assembly includes a patch installation frame having a self-expanding body extending between a proximal end and an open distal end and defining a lumen therethrough. The patch delivery assembly also includes a delivery cable having a distal end coupled to the proximal end of the patch installation frame and further defining the lumen, and a securement device extending through the lumen defined through the delivery cable and the patch installation frame, the securement device terminating in a distal working end including a securement mechanism. In a deployment configuration of the patch delivery assembly, the patch delivery assembly further includes a patch releasably coupled to the distal end of the patch installation frame, for securement to tissue of the target site using the securement mechanism.

20 Claims, 7 Drawing Sheets

(56)  References Cited

U.S. PATENT DOCUMENTS

| | | |
|---|---|---|
| 2009/0216264 A1 | 8/2009 | Friedman et al. |
| 2012/0316594 A1* | 12/2012 | Palese ................ A61B 17/0057 |
| | | 606/215 |
| 2017/0156853 A1 | 6/2017 | Weber et al. |
| 2019/0307331 A1 | 10/2019 | Saadat et al. |

\* cited by examiner

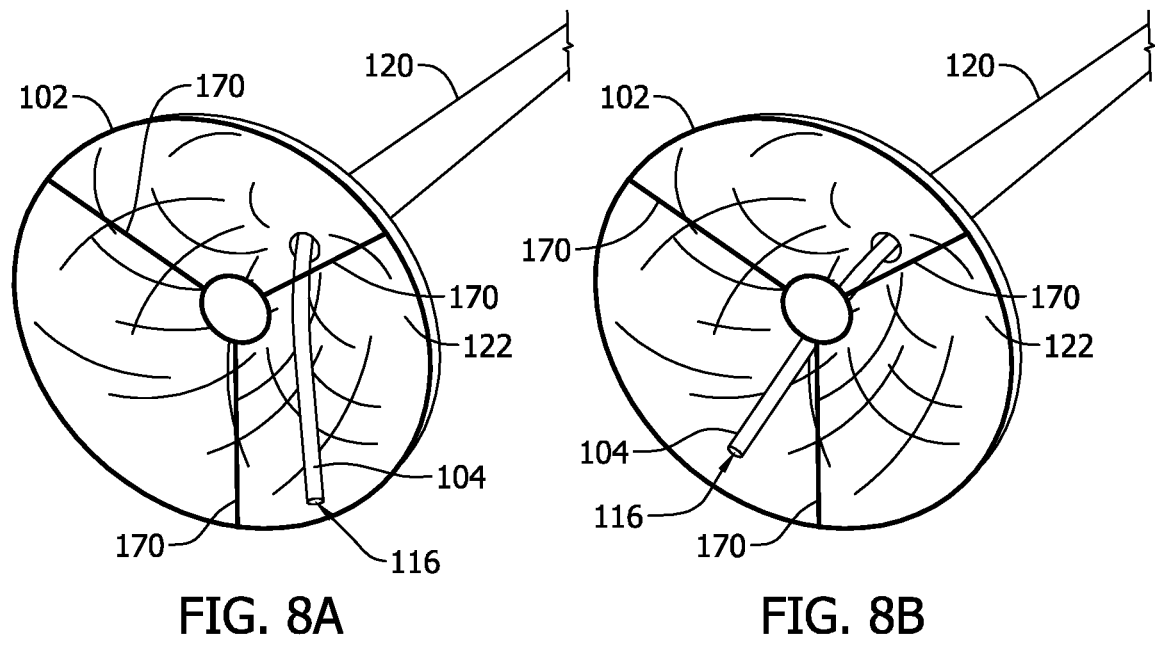
FIG. 8A                    FIG. 8B
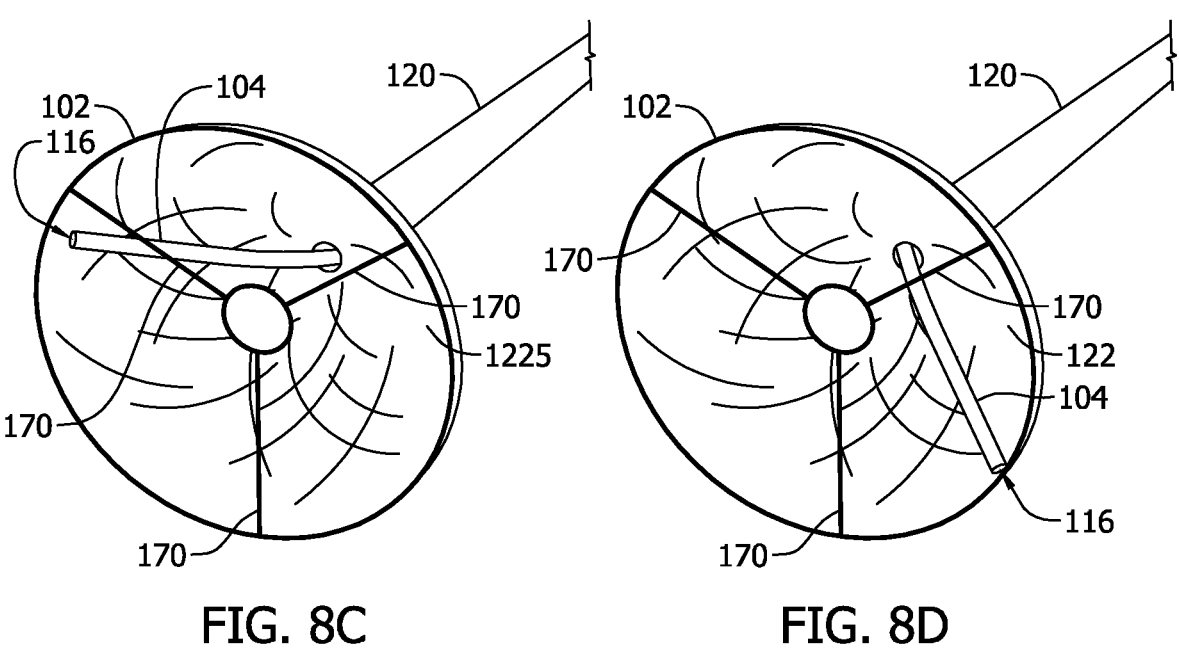
FIG. 8C                    FIG. 8D

ASSEMBLY AND METHOD FOR THE CLOSURE OF VASCULAR ABNORMALITIES

CROSS REFERENCE TO RELATED APPLICATIONS

The present application claims priority to U.S. Provisional Patent Application No. 63/414,158, filed Oct. 7, 2022, the disclosure of which is hereby incorporated by reference in its entirety as if fully set forth herein.

BACKGROUND OF THE DISCLOSURE

A. Field of Disclosure

The present disclosure relates generally to medical devices that are used in the human body. In particular, the present disclosure is directed to embodiments of a patch delivery assembly and methods of operating the same, to deploy and secure a patch at a vascular abnormality.

B. Background

An occluder is a medical device used to treat (e.g., occlude) tissue at a target site within the human body, such as an abnormality, a vessel, an organ, an opening, a chamber, a channel, a hole, a cavity, a lumen, or the like. For example, an occluder may be used to occlude or close an atrial septal defect (ASD), a ventricular septal defect (VSD), or a patent foramen ovale (PFO), which are generally characterized as holes in the subject tissue. Percutaneous and surgical procedures have been developed to deploy occluders—or other implantable devices—within these defects. In other instances, other defect closure devices, such as annuloplasty rings or valves secured to the subject tissue, have also been used.

However, it is recognized that employing these devices to close tissue defects may have various disadvantages, such as introducing foreign objects into the patient's body, tissue erosion, development or exacerbation of allergies (e.g., nickel allergies), and blood flow issues around the device.

SUMMARY OF THE DISCLOSURE

The present disclosure is directed to a patch delivery assembly for treating a target site. The patch delivery assembly includes a patch installation frame including a self-expanding body extending between a proximal end and an open distal end and defining a lumen therethrough. The patch delivery assembly also includes a delivery cable having a distal end coupled to the proximal end of the patch installation frame and further defining the lumen, and a securement device extending through the lumen defined through the delivery cable and the patch installation frame. The securement device terminates in a distal working end including a securement mechanism. In a deployment configuration of the patch delivery assembly, the patch delivery assembly further comprises a patch releasably coupled to the distal end of the patch installation frame, for securement to tissue of the target site using the securement mechanism.

The present disclosure is also directed to a method of securing a patch to tissue at a target site. The method includes positioning a patch delivery assembly at the target site, the patch delivery assembly including (i) a patch installation frame including a self-expanding body extending between a proximal end and an open distal end and defining a lumen therethrough, (ii) a delivery cable having a distal end coupled to the proximal end of the patch installation frame and further defining the lumen, and (iii) a securement device extending through the lumen defined through the delivery cable and the patch installation frame, the securement device terminating in a distal working end including a securement mechanism, wherein, in a deployment configuration of the patch delivery assembly, the patch delivery assembly further includes a patch releasably coupled to the distal end of the patch installation frame. The method also includes deploying the patch installation frame from a delivery catheter, the deploying including (a) expanding the patch installation frame from a constricted delivery configuration to an expanded deployment configuration and (b) simultaneously expanding the patch coupled to the patch installation frame. The method also includes abutting the distal end of the patch installation frame and the patch against tissue at the target site, securing the patch to the tissue using the securement mechanism, and de-coupling the patch from the patch installation frame.

BRIEF DESCRIPTION OF THE DRAWINGS

FIGS. 8A-8D depict views of the distal end of the patch delivery assembly to illustrate a range of motion of the securement device of the embodiment of the patch delivery assembly shown in FIGS. 6 and 7.

Corresponding reference characters indicate corresponding parts throughout the several views of the drawings. It is understood that that figures are not necessarily to scale.

DETAILED DESCRIPTION OF THE DISCLOSURE

The present disclosure relates generally to medical devices that are used in the human body. Specifically, the present disclosure provides a delivery assembly for delivering, deploying, and installing an occlusive patch at a target site (e.g., a tissue defect, such as a hole through tissue at the target site).

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

Although the exemplary embodiment of the medical device is described as treating a target site including a hole through the subject tissue, such as an atrial septal defect (ASD), a ventricular septal defect (VSD), a patent foramen *ovale* (PFO), or a left atrial appendage (LAA), as the medical device may be configured to treat any target site that could benefit from occlusion, such as an abnormality, a vessel, an organ, an opening, a chamber, a channel, a hole, a cavity, or the like, located anywhere in the body. Other physiological conditions in the body occur where it is also desirous to occlude a vessel or other passageway to prevent blood flow into or therethrough. These device embodiments may be used anywhere in the vasculature where the anatomical conditions are appropriate for the design.

As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed," "installed," "secured," and "implanted" may be used interchangeably herein.

The medical device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements Like numbers refer to like elements throughout.

Figure 1:
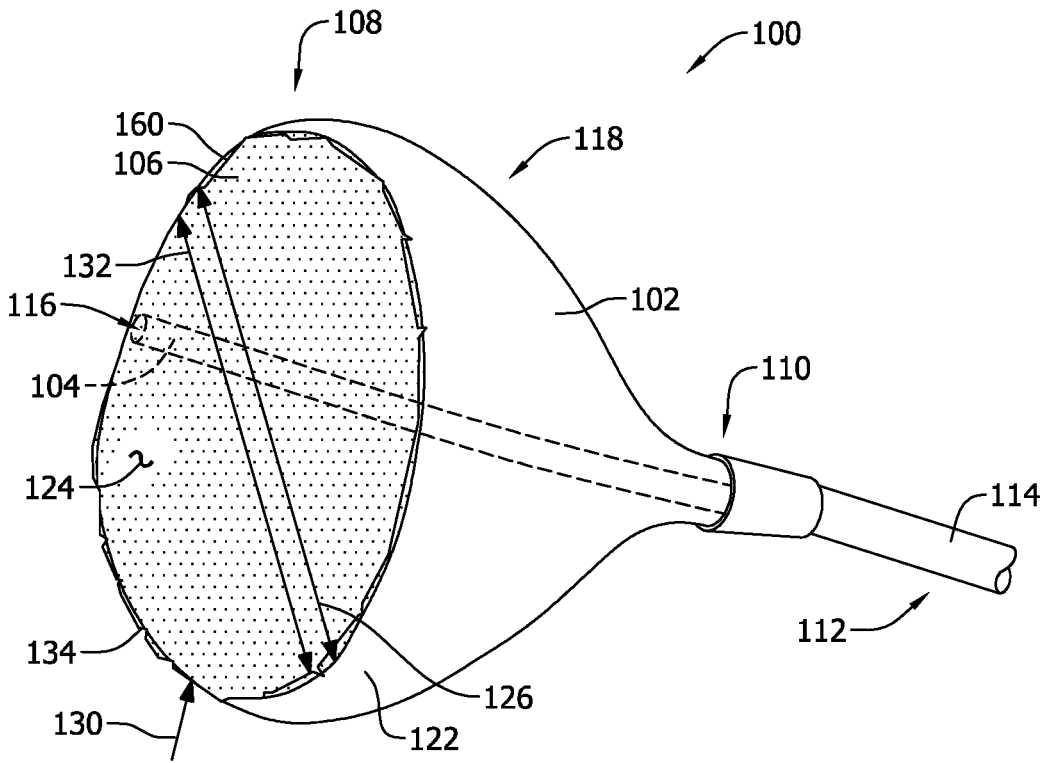
FIG. 1 depicts a first perspective view of a patch delivery assembly in accordance with the present disclosure, including a patch installation frame, a securement device, and a patch coupled to a distal end of the patch installation frame for deployment of the patch at a target site.
Figure 2:
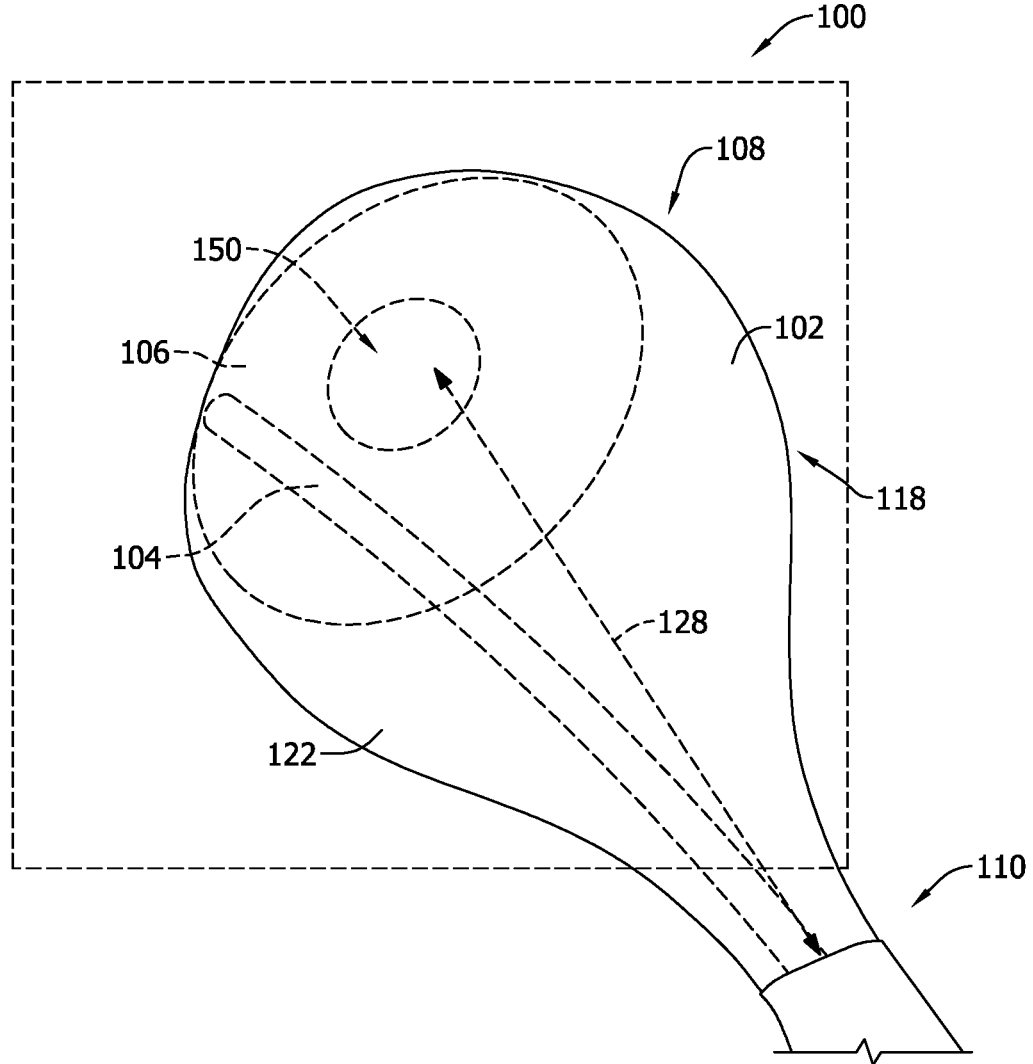
FIG. 2 depicts a second perspective view of the patch delivery assembly shown in FIG. 1, in which the patch is being secured to tissue at the target site.

Turning now to FIGS. 1 and 2, an example embodiment of a patch delivery assembly 100 is shown. Patch delivery assembly 100 includes a patch installation frame 102 and a securement device 104. In a delivery or deployment configuration, as shown in FIGS. 1 and 2, patch delivery assembly 100 also includes a patch 106, which is secured or coupled to a distal end 108 of patch installation frame 102, as described further herein.

A proximal end 110 of patch installation frame 102 is coupled to a distal end 112 of a delivery cable 114. Patch installation frame 102 and delivery cable 114 share a common lumen (not specifically shown) through which securement device 104 extends. Specifically, securement device 104 extends distally from a proximal end (not shown) of the lumen (not shown) through delivery cable 114 and patch installation frame 102 and terminates at a distal working end 116. Distal working end 116 includes a securement mechanism (not specifically shown) that facilitates securing patch 106 to tissue at a target site (e.g., to occlude a hole in the tissue at the target site using patch 106). For instance, distal working end 116 may include a suture mechanism, a staple mechanism, an adhesive mechanism, a thermal bonding mechanism, or any other mechanism (or combination thereof) suitable to secure patch 106 to the tissue at the target site.

Figure 3:
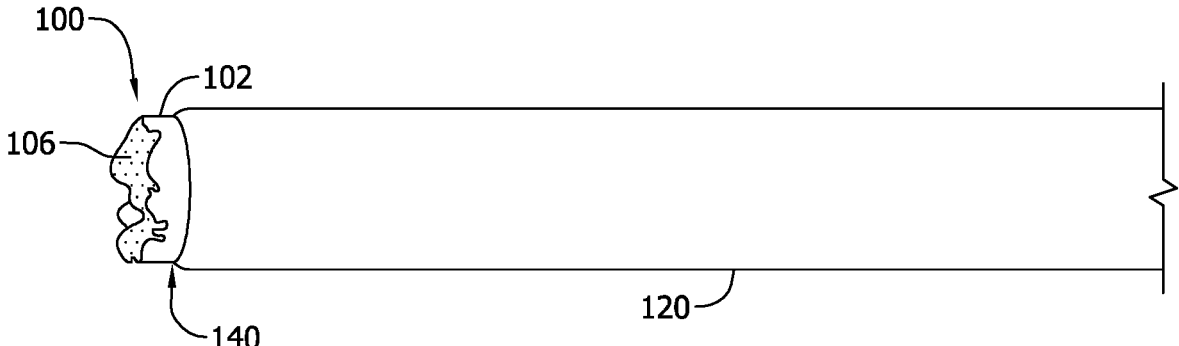
FIGS. 3 and 4 depict side views of deployment of the patch delivery assembly shown in FIG. 1.
Figure 4:
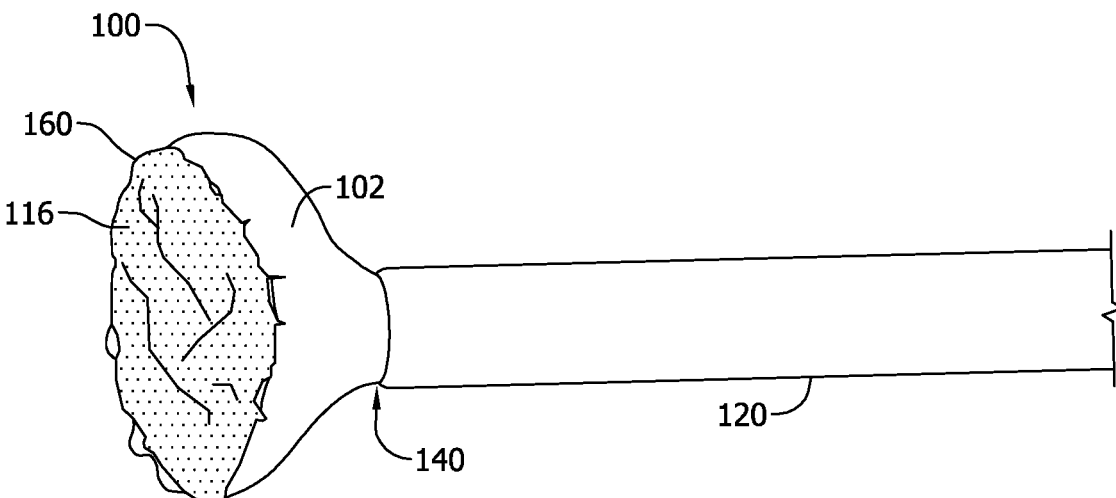
Figures 5A, 5B:
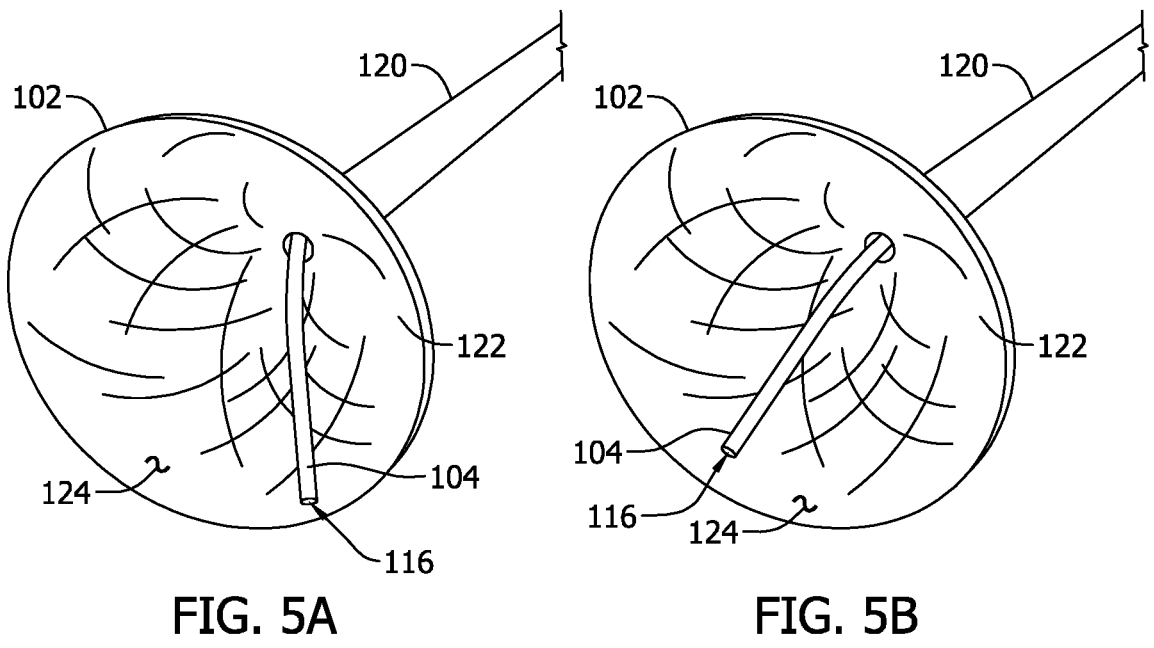
FIGS. 5A-5D depict views of the distal end of the patch delivery assembly to illustrate a range of motion of the securement device of the patch delivery assembly shown in FIG. 1.
Figures 5C, 5D:
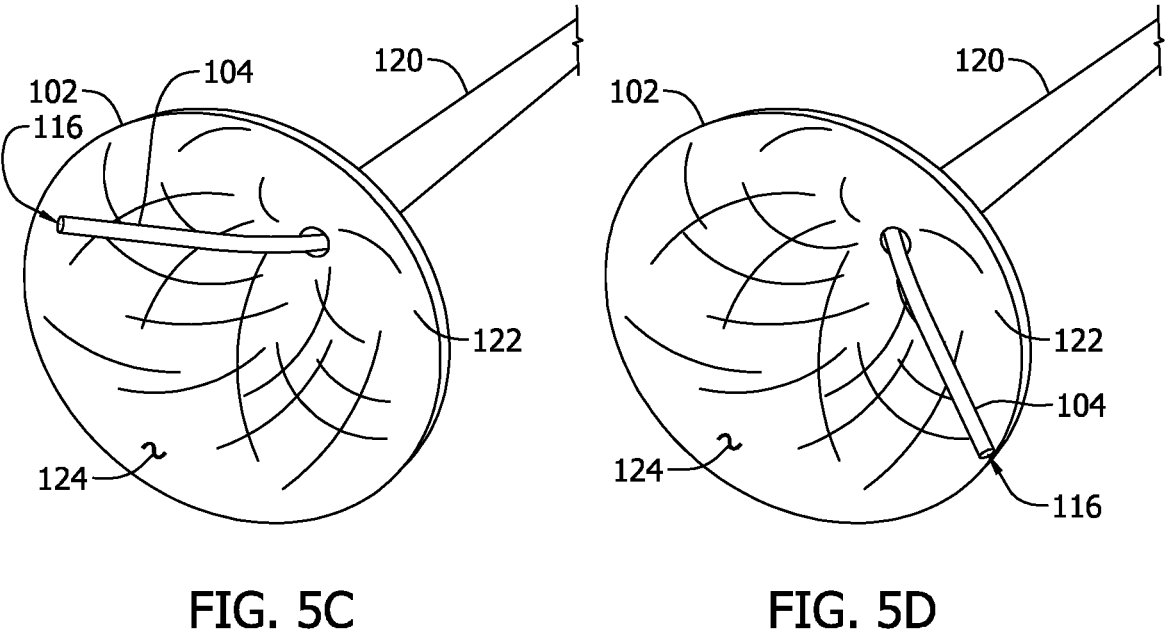

In one example embodiment, patch delivery assembly 100 is navigated to a patch installation site (e.g., a tissue defect 150, as shown in FIG. 2, also referred to herein as a target site) using a delivery catheter 120 (see FIGS. 3 and 4). For instance, delivery catheter 120 may be introduced to the patient's body via transfemoral insertion or any other suitable method. Patch installation frame 102 is constricted within delivery catheter 120 in a collapsed or contracted delivery configuration, shown partially in FIG. 3. Once at the patch installation site (e.g., tissue defect 150), patch installation frame 102 is advanced from a distal end 140 of delivery catheter 120, as shown in FIG. 4. For example, delivery cable 114 may be advanced distally through delivery catheter 120 and/or delivery catheter 120 may be withdrawn proximally while maintaining a position of patch installation frame 102.

Once deployed from delivery catheter 120, patch installation frame 102 expands to an expanded, installation configuration, as shown in FIGS. 1 and 2. As patch installation frame 102 expands, so too does patch 106. Specifically, because patch 106 is coupled to distal end 108 of patch installation frame 102, patch 106 is expanded to an installation configuration upon deployment and expansion of patch installation frame 102. In the installation configuration, patch 106 is maintained under tension and in a desired installation position by patch installation frame 102.

Patch installation frame 102 defines a confined securement path or area about which distal working end 116 of securement device 104 is maneuverable relative to distal end 108 of patch installation frame 102 and, thereby, relative to patch 106. Distal working end 116 of securement device 104 is maneuverable relative to patch installation frame 102, as described in greater detail herein, to secure (e.g., suture, staple, adhere, etc.) patch 106 to the tissue at the target site, using the associated securement mechanism.

Once patch 106 is secured to the tissue, patch 106 provides an occlusive effect; that is, patch 106 blocks or substantially blocks blood flow therethrough. Patch 106 is then decoupled from patch installation frame 102, as described further herein, and patch delivery assembly 100 (now including no patch) is retracted into delivery catheter 120 and withdrawn from the target site. Patch 106 remains secured to tissue at the target site, providing an occlusive or substantially occlusive effect while minimizing an amount of material introduced into the patient's body (e.g., limited to patch 106 and any material(s) securing patch 106 to the tissue). Moreover, patch 106 has a significantly reduced profile compared to other known occlusive devices, and therefore limits bulging around the tissue defect and any associated blood flow effects thereof.

In the illustrated embodiment of patch delivery assembly 100, patch installation frame 102 has a tapered shape in its deployed or expanded configuration. Specifically, patch installation frame 102 includes a body 118 that tapers outwardly from proximal end 110 to distal end 108 thereof. Thereby, body 118 of patch installation frame 102 has a "cone" shape, which can have convex (see FIGS. 1 and 2) or concave (see FIGS. 5A-5D) walls 122, or, in still other embodiments, generally straight tapered walls 122. The walls 122 of body 118 define a cavity 124 therewithin. In the illustrated embodiment of patch installation frame 102, distal end 108 is "open," when patch 106 is not coupled thereto. That is, patch installation frame 102 is formed with an open, unobstructed distal end 108 free of the material forming patch installation frame 102, to enable securement device 104 to readily access patch 106 without interfering material. In some embodiments, cavity 124 may contain a nesting structure (not shown) to help support and guide securement device 104, such as, but not limited to, a nesting nitinol braided structure.

Body 118 of patch installation frame 102, in its expanded configuration, has a distal diameter 126 and a corresponding distal circumference 130. Distal diameter 126 may vary, depending on the application thereof (e.g., depending on a size, a shape, or a configuration of tissue defect 150). Distal diameter 126 is sized such that patch 106 will cover tissue defect 150. For example, distal diameter 126 may be about 4 mm up to about 40 mm, and may accommodate patch 106 having a patch diameter 132 of, for example, 10 mm to 50 mm, or up to 60 mm in some embodiments. Patch 106 may be sized such that patch 106 is larger, smaller, or substantially similar in size as patch installation frame 102 (e.g., patch diameter 132 may be larger, smaller, or substantially similar in size to distal diameter 126). Body 118 of patch installation frame 102 also has a length 128 (see FIG. 2), defined along a longitudinal axis thereof. The length 128 is sized such that distal end 108 may expand and reach its full diameter (e.g., distal diameter 126). Therefore, depending upon the appropriate distal diameter for the application, length 128 may vary.

In some embodiments, length 128 is related to distal diameter 126 in accordance with a predefined ratio. For example, the predefined ratio of length 128 to distal diameter 126 may range from about 0.5:1 to 4:1. In some embodiments, the predefined ratio of length 128 to distal diameter 126 may be 1:1. The predefined ratio of length 128 to distal diameter 126 may depend on the size of patch 106, with patch 106 having a diameter in a range of about 10 mm to about 54 mm. For example, the predefined ratio of length 128 to distal diameter 126 of 4:1 may be available for patch 106 having the 54 mm diameter.

In one example embodiment, patch installation frame 102 is formed from a shape-memory material, such that patch installation frame 102 expands to its expanded configuration upon deployment thereof. In one particular embodiment, patch installation frame 102 is formed from a braided metallic shape-memory material, such as nitinol. For example, patch installation frame 102 may be formed from an insulated nitinol material, such as, but not limited to, a 72 strand nitinol material with 6 strands being conductive to facilitate patch suture release. It is also understood that patch installation frame 102 may be formed from various materials other than nitinol that have elastic properties, such as stainless steel, trade named alloys such as Elgiloy®, or Hastalloy, Phynox®, MP35N, CoCrMo alloys, metal, polymers, or a mixture of metal(s) and polymer(s). Suitable polymers may include PET (Dacron™), polyester, polypropylene, polyethylene, HDPE, Pebax™, nylon, polyurethane, silicone, PTFE, polyolefins and ePTFE. Additionally, it is contemplated that patch installation frame 102 may comprise any material that has the desired elastic properties to ensure that the frame may be deployed to its expanded configuration and recaptured in a manner disclosed within this application.

In one particular embodiment, patch installation frame 102 is formed by folding the shape memory material upon itself, such that the fold defines distal end 108 of patch installation frame 102 (also referred to as distal end 108 of body 118). In some such instances, the shape memory material is initially formed as a braided tubular structure, which is cut to a desired length, folded upon itself, and heat-set over a mandrel to define the expanded configuration thereof. The free ends of the braided, folded shape-memory material, at proximal end 110 of patch installation frame 102 (also referred to as proximal end 110 of body 118), may be welded, crimped, adhered, or otherwise stabilized to prevent unraveling of the braided shape-memory material. In some embodiments, proximal end 110 of patch installation frame 102 is coupled to distal end 112 of delivery cable 114 after the free ends of the braided material have already been fixed. In other embodiments, the free ends of the braided material at proximal end 110 of patch installation frame 102 are simultaneously fixed and secured to distal end 112 of the delivery cable 114. Proximal end 110 of patch installation frame 102 (e.g., including the free ends of the folded, braided shape-memory material) is coupled to distal end 112 of delivery cable 114 by adhesive, welding, melting, overmolding, internal molding, or any other suitable attachment method. In at least some embodiments, the free ends of the braided, folded shape-memory material are coupled to an exterior surface of delivery cable 114, such that the free ends do not interfere with any components positioned within delivery cable 114 (e.g., securement device 104).

Additionally, proximal end 110 of patch installation frame 102 defines a lumen or channel therethrough (not specifically shown). In the example embodiment, this lumen is shared with (e.g., is continuous with) a lumen defined through delivery cable 114 (not specifically shown). Accordingly, various components, such as securement device 104, can be advanced through the lumen and into cavity 124 of patch installation frame 102.

Patch 106 is coupled to distal end 108 of patch installation frame 102. In some embodiments, patch 106 is coupled to patch installation frame 102 along the fold that forms distal end 108 of patch installation frame 102. In other embodiments, patch 106 is coupled interior to or exterior to the fold. Patch 106 may be comprised of any suitable flexible and occlusive material that allows for patch 106 to provide a sealing, occlusive effect. Examples of suitable material may include, but are not limited to, polyester, polyethylene, polytetrafluoroethylene (PTFE), expanded polytetrafluoroethylene (ePFTE), decellularized extracellular matrix (ECM), Dacron™, and xenograft pericardium, such as bovine pericardium.

In one or more embodiments, patch 106 also includes a radiopaque material coupled thereto. The radiopaque material is visible under fluoroscopy and enables (1) verifying the position of patch 106 during deployment and securement thereof, and (2) identification or confirmation of the position of patch 106 at some later date, such as during check-ups or before some other kind of medical intervention. In some such embodiments, a marker of radiopaque material (e.g., a radiopaque marker) is positioned at or along the circumference of patch 106. For example, a plurality of discrete radiopaque markers may be attached to (e.g., sutured or sewn to) an outer edge 160 of patch 106 at regular intervals, to identify the perimeter of patch 106 under fluoroscopy. Alternatively, a wire or thread formed from radiopaque material may be attached to (e.g., sutured or sewn to, woven into, etc.) the entire outer edge of patch 106. In still other embodiments, patch 106 may be impregnated with the radiopaque material.

Patch 106 has a shape and size that generally corresponds to a shape and size of distal end 108 of patch installation frame 102, because patch installation frame 102 is configured to maintain patch 106 in a taut, tensioned configuration upon deployment and during securement of patch 106 to the tissue. That is, where patch installation frame 102 has a circular distal end 108, patch 106 may be circular as well. The patch diameter 132 of patch 106, and the corresponding circumference, is such that the patch 106 covers tissue defect 150. For example, diameter 126 may be about 10 mm to about 60 mm, in different embodiments, and a corresponding circumference. In some embodiments, patch diameter 132 of patch 106 is substantially the same as distal diameter 126 of distal end 108 of patch installation frame 102 in its expanded configuration. In some other embodiments, patch diameter 132 of patch 106 is slightly smaller than distal diameter 126, to ensure patch 106 is fully stretched when patch installation frame 102 expands. In still other embodiments, patch diameter 132 of patch 106 is larger than distal diameter 126, but patch 106 is coupled to patch installation frame 102 along a path radially interior of the circumference of patch 106 (e.g., the radial distance around the outer edge 160 of patch 106), such that patch installation frame 102 still maintains patch 106 in a taut configuration upon deployment.

It should be readily understood that although the shape of patch 106, and distal end 108 of patch installation frame 102, are depicted and generally described as round or circular, other shapes or configurations are contemplated within the scope of the present disclosure. For example, patch 106 and/or distal end 108 of patch installation frame 102 may have an oval shape, a square/rectangular shape, a crescent shape, or any other regular or irregular shape. The selected shape may depend, in some instances, on the shape or size of the defect to be occluded. In some embodiments, a circular or round patch 106 may be selected, with overall dimensions to fully cover the defect, regardless of its shape. In other cases, a patch 106 may be selected that has a shape more closely corresponding to a shape of the defect to be covered. References to "diameter," circumference," and the like may therefore be broadly interpreted to cover other similar dimensions, for shapes other than round/circular.

In the example embodiment, patch 106 is coupled to patch installation frame 102 by one or more threads of suture material 134. In some embodiments, patch 106 may be coupled to patch installation frame 102 by a single continuous thread of suture material 134. In other embodiments, patch 106 may be coupled to patch installation frame 102 by a plurality of suture threads of a smaller length than the single continuous thread, with each of the plurality of suture threads cut and pulled through to facilitate smoother bunching. Suture material 134 couples patch 106 to patch installation frame 102 along the circumference of patch installation frame 102. In some embodiments, one or both free ends (not shown) of suture material 134 extends proximally through the lumen (not shown) of patch installation frame 102 and delivery cable 114 (e.g., to a handle of patch delivery assembly 100, not shown). In such cases, once patch 106 is secured to the tissue, as described herein, suture material 134 is trimmed by an operator and is thereby de-threadable from patch 106 and patch installation frame 102 for withdrawal, in a single piece, from the target site. In other instances, securement device 104 may be withdrawn from the target site, and a detachment device may be advanced to the target site (e.g., through the lumen). The detachment device may cut suture material 134 or otherwise decouple the patch from the patch installation frame 102. In still other instances, suture material 134 holding patch 106 may be ablated to remove the suture. For example, electrical energy may be applied to patch installation frame 102 to burn off suture material 134 and release patch 106. It is contemplated that patch 106 may be otherwise coupled to patch installation frame 102 in a detachable manner, via adhesive(s), staple(s), etc.

As described herein, securement device 104 extends through the lumen defined through the delivery cable 114 and the patch installation frame 102. In the example embodiment, distal working end 116 of securement device 104 not only includes the corresponding securement mechanism, but also is deflectable, rotatable, and/or otherwise steerable. For instance, a proximal end of securement device 104 (not shown) is coupled to a handle or other operator interface of patch delivery assembly 100. In response to operation of one or more controls, distal working end 116 of securement device 104 may deflect and/or rotate.

As shown in FIGS. 5A-5D, in the example embodiment, distal working end 116 is deflectable and rotatable (e.g., "steerable") with a 360° range of motion. In particular, distal working end 116 is steerable throughout cavity 124 of patch installation frame 102 and, more specifically, along the circumference thereof. That is, distal end 108 of patch installation frame 102 confines distal working end 116 of securement device 104 within cavity 124 thereof, and defines a securement path for distal working end 116 (e.g., along an interior surface of the circumference of distal end 108). Securement device 104 may also be activated in response to operation of one or more controls, such that the corresponding securement mechanism on distal working end 116 is activated to secure patch 106 to adjacent tissue as distal working end 116 is steered along the securement path. Thereby, patch 106 is secured to the tissue at the target site.

Thereafter, as described above, patch 106 is decoupled from patch installation frame 102, and patch delivery assembly 100 (sans patch 106) is retracted and withdrawn from the target site. Patch 106 remains coupled to the tissue, providing an immediate occlusive or substantially occlusive effect.

In some embodiments, patch delivery assembly 100 is deliverable through a 12 Fr delivery catheter (e.g., delivery catheter 120, shown in FIGS. 3 and 4). In particular, patch delivery assembly 100 may be configured such that the profile of patch installation frame 102 and/or patch 106 is deliverable through a 12 Fr delivery catheter. Moreover, in the example embodiment, patch delivery assembly 100 is sized such that securement device 104 is extendable through the lumen of patch installation frame 102 and delivery cable 114. In some embodiments, patch installation frame 102 and/or patch 106 may have a reduced profile. For example, patch delivery assembly 100 may be deliverable through a delivery catheter of less than 12 Fr, such as from about 6 Fr to about 12 Fr. In other embodiments, patch installation frame 102 and/or patch 106 may have an expanded profile. For example, patch delivery assembly 100 may be deliverable through a delivery catheter of more than 12 Fr, such as from about 12 Fr to about 16 Fr.

Figure 6:
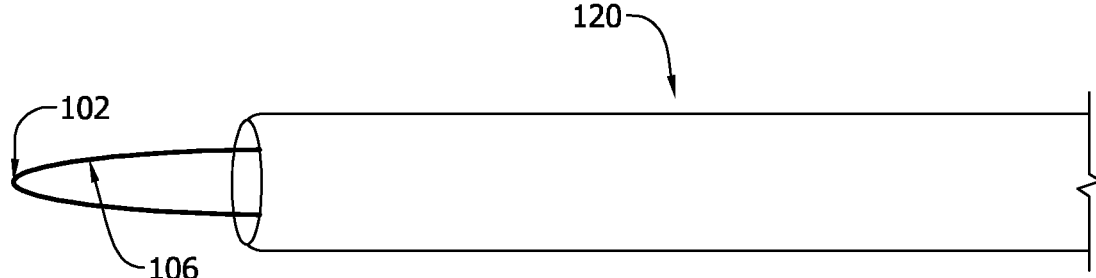
FIGS. 6 and 7 depict side views of deployment of an alternative embodiment of a patch delivery assembly.
Figure 7:
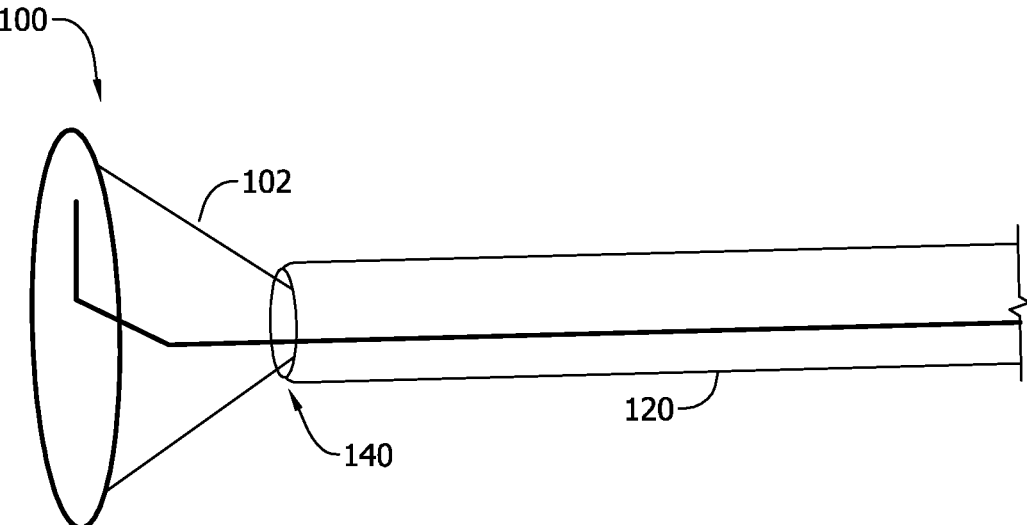

FIGS. 6 and 7 depict side views of deployment of an alternative embodiment of patch delivery assembly 100 using the delivery catheter 120. In the illustrated alternative embodiment of patch delivery assembly 100, patch installation frame 102 has a wheel shape in its deployed or expanded configuration. Specifically, body 118 of patch installation frame 102 has a circular shape with one or more inner spokes 170. The one or more inner spokes 170 may facilitate increased radial strength of patch installation frame 102. Distal working end 116 of securement device 104 is maneuverable relative to patch installation frame 102, for insertion between the one or more inner spokes 170 of the wheel shape of patch installation frame 102.

FIGS. 8A-8D depict views of the distal end of the patch delivery assembly to illustrate a range of motion of the securement device of the embodiment of the patch delivery assembly shown in FIGS. 6 and 7. In the illustrated alternative embodiment of patch delivery assembly 100, patch installation frame 102 is formed having higher edges to facilitate improved maneuverability of securement device 104 due to an increase in space to engage the tissue.

Figure 9:
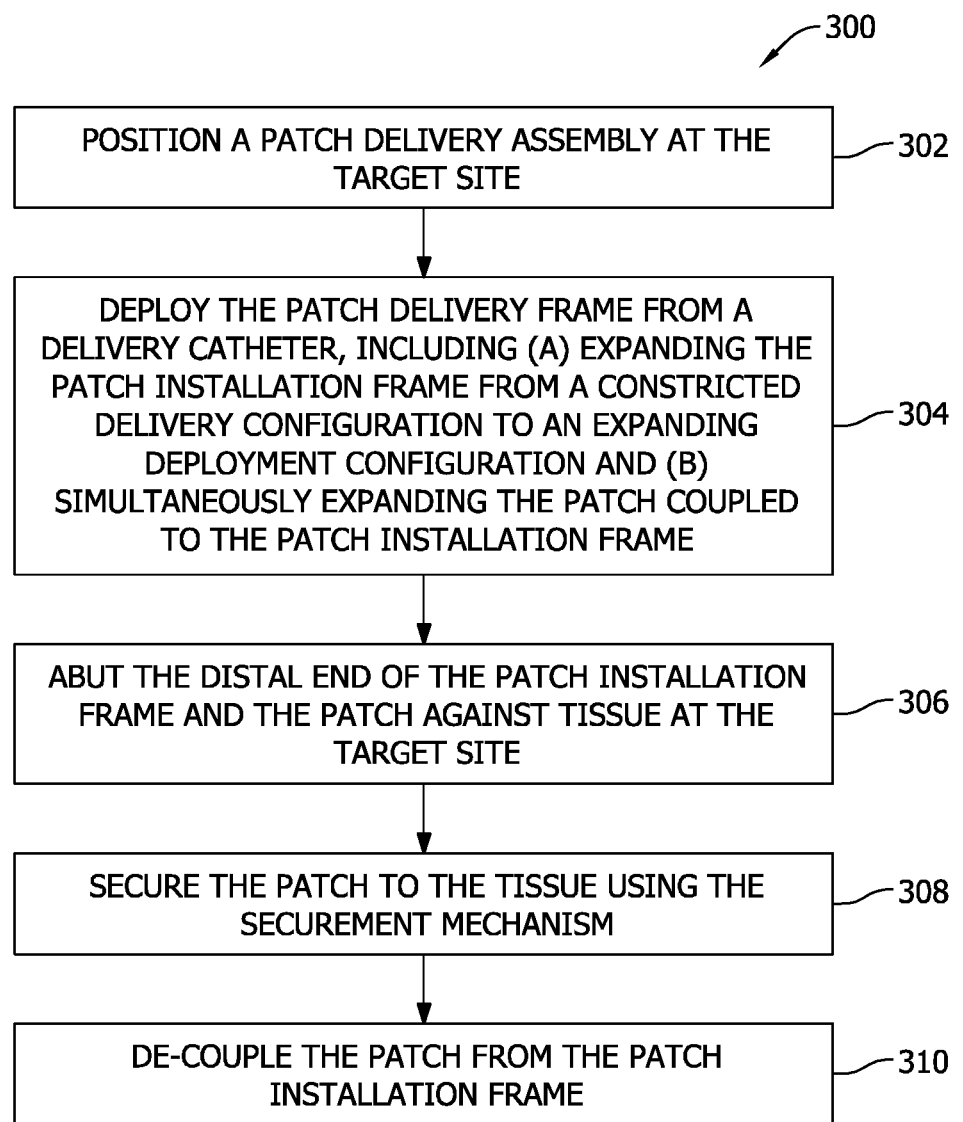
FIG. 9 is a flow diagram of a method of securing a patch to tissue at a target site in accordance with the present disclosure.

Turning now to FIG. 9, a flow diagram of an exemplary method 300 for deploying a patch (e.g., patch 106) at a target site is illustrated. In the exemplary embodiment, method 300 includes positioning 302 a patch delivery assembly (e.g., patch delivery assembly 100) at the target site. The patch delivery assembly may include (i) a patch installation frame (e.g., patch installation frame 102) including a self-expanding body extending between a proximal end and an open distal end and defining a lumen therethrough, (ii) a delivery cable (e.g., delivery cable 114) having a distal end coupled to the proximal end of the patch installation frame and further defining the lumen, and (iii) a securement device (e.g., securement device 104) extending through the lumen defined through the delivery cable and the patch installation frame. The securement device terminates in a distal working end including a securement mechanism. In a deployment configuration of the patch delivery assembly, the patch delivery assembly may further include a patch releasably coupled to the distal end of the patch installation frame.

Method 300 also includes deploying 304 the patch installation frame from a delivery catheter. Deploying 304 the patch installation frame includes (a) expanding the patch installation frame from a constricted delivery configuration to an expanded deployment configuration and (b) simultaneously expanding the patch coupled to the patch installation frame.

Method 300 further includes abutting 306 the distal end of the patch installation frame and the patch against tissue at the target site, securing 308 the patch to the tissue using the securement mechanism, and de-coupling 310 the patch from the patch installation frame.

Method 300 may include additional, alternative, and/or fewer steps, including those described herein. In some embodiments, securing 308 includes rotating the securement mechanism through a 360° securement path defined by the distal end of the patch installation frame. Securing 308 may include suturing, adhering, or stapling the patch to the tissue using the securement mechanism. In other embodiments, de-coupling 310 may include trimming a one or more threads of suture material coupling the patch to the distal end of the patch installation frame.

In some embodiments, method 300 may include coupling the patch to the patch installation frame prior to positioning 302, which may include threading one or more threads of suture material about a circumference of the distal end of the patch installation frame and through the patch. In some instances, deploying 304 includes proximally retracting the delivery catheter, and/or distally advancing the delivery cable through the delivery catheter.

Moreover, in some embodiments, method 300 may include verifying a position of the patch delivery assembly prior to securing 308 the patch. This verifying may include, for example, performing contrast injection(s) under fluoroscopy, to verify the device is in the proper location and the defect is covered prior to securing the patch. Additionally or alternatively, verifying may include detecting any radiopaque material coupled to and/or integrated into the patch. In some embodiments, method 300 may further include withdrawing the patch delivery assembly from the target site while leaving the patch secured to the tissue at the target site.

While embodiments of the present disclosure have been described, it should be understood that various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A patch delivery assembly for treating a target site, the patch delivery assembly comprising:
   a patch installation frame comprising a self-expanding body extending between a proximal end and an open distal end and defining a lumen therethrough;
   a delivery cable having a distal end coupled to the proximal end of the patch installation frame and further defining the lumen; and
   a securement device extending through the lumen defined through the delivery cable and the patch installation frame, the securement device terminating in a distal working end including a securement mechanism,
   wherein, in a deployment configuration of the patch delivery assembly, the patch delivery assembly further comprises a patch releasably coupled to the distal end of the patch installation frame, for securement to tissue of the target site using the securement mechanism,
   wherein the patch installation frame comprises a folded braided shape-memory material and has a tapered wall defining a cavity therein.

2. The patch delivery assembly of claim 1, wherein the patch comprises a flexible occlusive material.

3. The patch delivery assembly of claim 1, wherein the securement mechanism comprises one of a suture mechanism, an adhesive mechanism, and a staple mechanism.

4. The patch delivery assembly of claim 1, wherein a shape of the patch corresponds to a shape of the distal end of the patch installation frame.

5. The patch delivery assembly of claim 1, wherein the distal end of the patch installation frame is open and forms an opening which is free of a material forming the patch installation frame.

6. The patch delivery assembly of claim 5, wherein the distal end of the patch installation frame defines a securement path that is configured to confine operation of the securement mechanism therewithin.

7. The patch delivery assembly of claim 1, wherein the securement device is rotatable within a 360° range of motion.

8. The patch delivery assembly of claim 1, wherein the patch installation frame has a tapered cone shape with the patch installation frame tapering outwardly from the proximal end towards the distal end thereof.

9. The patch delivery assembly of claim 1, wherein a fold in the folded braided shape-memory material defines the distal end of the patch installation frame.

10. The patch delivery assembly of claim 1, wherein the folded braided shape-memory material forming the patch installation frame includes free ends at the proximal end of the patch installation frame, the free ends being welded, crimped, or adhered to prevent unraveling of the folded braided shape-memory material.

11. The patch delivery assembly of claim 10, wherein the free ends of the folded braided shape-memory material are coupled to an exterior surface of the delivery cable.

12. A method of securing a patch to tissue at a target site, the method comprising:

positioning a patch delivery assembly at the target site, the patch delivery assembly including (i) a patch installation frame including a self-expanding body extending between a proximal end and an open distal end and defining a lumen therethrough, (ii) a delivery cable having a distal end coupled to the proximal end of the patch installation frame and further defining the lumen, and (iii) a securement device extending through the lumen defined through the delivery cable and the patch installation frame, the securement device terminating in a distal working end including a securement mechanism, wherein, in a deployment configuration of the patch delivery assembly, the patch delivery assembly further includes a patch releasably coupled to the distal end of the patch installation frame, wherein the patch installation frame comprises a folded braided shape-memory material and has a tapered wall defining a cavity therein;

deploying the patch installation frame from a delivery catheter, said deploying comprising (a) expanding the patch installation frame from a constricted delivery configuration to an expanded deployment configuration and (b) simultaneously expanding the patch coupled to the patch installation frame;

abutting the distal end of the patch installation frame and the patch against tissue at the target site;

securing the patch to the tissue using the securement mechanism; and de-coupling the patch from the patch installation frame.

13. The method of claim 12, wherein said de-coupling the patch comprises trimming one or more suture materials coupling the patch to the distal end of the patch installation frame.

14. The method of claim 12, wherein said securing the patch comprises rotating the securement mechanism through a 360° securement path defined by the distal end of the patch installation frame.

15. The method of claim 12, wherein said securing the patch comprises one of suturing, adhering, and stapling the patch to the tissue using the securement mechanism.

16. The method of claim 12, further comprising withdrawing the patch delivery assembly from the target site while leaving the patch secured to the tissue at the target site.

17. The method of claim 12, further comprising verifying a position of the patch delivery assembly prior to said securing the patch.

18. The method of claim 12, further comprising coupling the patch to the patch installation frame prior to said positioning, said coupling comprising threading one or more suture materials about a circumference of the distal end of the patch installation frame and through the patch.

19. The method of claim 12, wherein said deploying the patch installation frame comprises proximally retracting the delivery catheter.

20. The method of claim 12, wherein said deploying the patch installation frame comprises distally advancing the delivery cable through the delivery catheter.

\* \* \* \* \*